United States Patent [19]

Guschl

[11] 4,094,856
[45] June 13, 1978

[54] FLAME RETARDANT POLYMERIC COMPOSITIONS

[75] Inventor: Randolph Joseph Guschl, Wilmington, Del.

[73] Assignee: E. I. Du Pont de Nemours and Company, Wilmington, Del.

[21] Appl. No.: 696,278

[22] Filed: Jun. 15, 1976

[51] Int. Cl.² ............................................. C08K 5/16
[52] U.S. Cl. .......................... 260/45.9 NP; 260/47 R; 260/927 N; 428/921
[58] Field of Search ................... 260/45.9 NP, 927 N, 260/47 P

[56] References Cited

U.S. PATENT DOCUMENTS

| | | | |
|---|---|---|---|
| 3,153,663 | 10/1964 | Sirrenberg et al. | 260/461 |
| 3,194,787 | 7/1965 | Redfarn et al. | 260/47 P |
| 3,226,355 | 12/1965 | Singleton et al. | 260/42.28 |
| 3,322,859 | 5/1967 | Sherr et al. | 260/45.9 NP |
| 3,468,981 | 9/1969 | Bezman | 260/927 N |
| 3,641,193 | 2/1972 | Frank et al. | 260/830 P |
| 3,795,526 | 5/1974 | Bergeron | 260/927 N |
| 3,839,513 | 10/1974 | Patel | 260/927 N |

FOREIGN PATENT DOCUMENTS 1,514,366   2/1968   France.

OTHER PUBLICATIONS

Fire Retardants by Lyons, (1970), pp. 37, 40, 41, 181–185.

*Primary Examiner*—V.P. Hoke

[57] ABSTRACT

Oligomers of (substituted phenoxy)cyclotriphosphazenes and aromatic diols render polymers such as polyesters, polyolefins, etc., in the form of fibers, films and other shapes permanently flame retardant.

15 Claims, No Drawings

FLAME RETARDANT POLYMERIC COMPOSITIONS

BACKGROUND OF THE INVENTION

With the discovery of polymer chemistry the fabric and film industries were revolutionized. Although many useful man-made compositions were developed to improve the quality of life in general, the search for polymeric compositions with improved properties has been a continual one. It has long been recognized that polymeric products, particularly fibers, films, fabrics and molded articles, when subject to excessive heat or contact with open flame, could be improved by imparting flame retardant properties to such products. The art of treating polymers is replete with attempts to reduce the flammability of such products.

Approaches such as coating the article, adding a flame retardant compound during polymerization, or incorporating the retardant in the polymer after polymerization have been attempted with various levels of success.

Perhaps the most common approach to treating articles such as polymeric fibers, films and fabrics has been to coat the article with a substance that would render the article resistant to burning. Such coatings are often removed during the useful life of the article by being worn off or washed out.

Incorporating the flame retardant material into the article itself appears to hold the most promise for the future; however, this approach has often been unsucessful due to undesirable changes in the properties of the finished polymer as a result of the flame retardant additive.

It has been observed that the mechanical properties, such as tensil strength, or the color of polymer in which flame retardant is incorporated may be adversely affected. In certain cases compatibility of the flame retardant with the polymer may be affected by processing conditions. For example, normal heat treatment or dyeing of fibers may cause the flame retardant to migrate to the surface of the polymer, thereby reducing the acceptability, in commerce, of the treated fiber. In addition the presence of certain flame retardant compositions in the polymer may corrode or otherwise adversely affect equipment employed to spin or shape the polymer into useful forms.

It has now been discovered that oligomers of (substituted phenoxy)cyclotriphosphazenes and aromatic diols when incorporated into polymeric compositions render such compositions flame retardant without significant adverse effect on the useful properties of the polymeric compositions.

Polymeric cyclotriphosphazenes are described in U.S. Pat. No. 3,711,542.

SUMMARY OF THE INVENTION

This invention relates to compounds of the formula

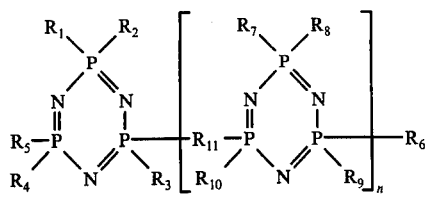

I wherein each of $R_1$ to $R_{10}$ is a substituent of the formula

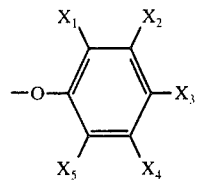

wherein $X_1$ to $X_5$ is hydrogen, bromine and chlorine, $R_{11}$ is a linking group derived from bisphenol A, resorcinol, hydroquinone, bisphenol S and p,p'-dihydroxybiphenyl, and $n$ is the number 1 or greater.

This invention also relates to the above compounds incorporated in a polymer selected from the group consisting of polyesters, polyamindes, polycaprolactam, acrylics, polyolefins, polycarbonates, epoxy resins, polyurethanes and polyphenylene oxides.

DESCRIPTION OF THE INVENTION

The present invention provides polymeric compositions possessing improved flame retardant properties.

In this specification flame retardance is used to describe the reduced tendency of a polymeric composition containing an oligomer of (substituted phenoxy)cyclotriphosphazenes and aromatic diols, hereafter called oligomer(s), to burn when the composition is ignited in a flame which is subsequently withdrawn when compared to the polymer which has the oligomer incorporated therein.

This invention relates to polymeric compositions containing a flame-retardant effective amount of an oligomer of Formula I. As indicated above, for purposes of this invention a flame-retardant effective amount of oligomer is that amount of cyclotriphosphazeneoligomer which when combined with a polymer will reduce the tendency of the polymer to burn when exposed to a flame. In general, from 1 to 30% by weight of oligomer when combined with a polymer will render the polymeric composition flame retardant. The actual amount of oligomer employed depends upon the polymer component of the composition and the end use in which the composition will be employed. It will be understood that from 3 to 25% by weight of oligomer is effective in polyester compositions, from 1 to 30% by weight of oligomer is effective in polyolefin, from 0.5 to 12% by weight of oligomer is effective in polyamide, from 5 to 30% by weight of oligomer is effective in ABS, from 5 to 35% by weight of oligomer is effective in acrylic and from 5 to 15% by weight of oligomer is effective in modacrylic.

The oligomer components of the compositions of this invention are generally glassy solids at room temperature, colorless, odorless and nontoxic. Further, the oligomers of this invention are thermally stable under the normal processing conditions employed in the manufacture of polymeric films, fibers and fabrics. For purposes of this specification thermally stable means the oligomer does not degrade under normal polymer processing, such as in preparing melt or solution of the polymer which is employed in spinning fibers; extruding films; or weaving and dyeing of fabrics. The oligomer component of the claimed composition is nonvolatile, photostable and economic to use.

The compositions of this invention are durable, for example, when treated fibers are woven into fabric, the fabric retains its flame retardant properties for at least 50 home launderings and the fabric is not discolored by exposure to u.v. light. A still further advantage is that the flame retardant is incorporated during normal processing of the polymer and does not require either a change in polymerization chemistry or an aftertreatment of the polymer composition.

An outstanding property of polymeric compositions of this invention which contain oligomer is the retention of the integrity of the composition even after being subjected to commercial heat and/or dyeing treatments. The oligomer remains thoroughly dispersed throughout the composition and no migration to the surface of polymers such as polyethylene is observed, thereby enabling the polymeric compositions of this invention to withstand the most vigorous treatments now used in processing untreated conventional polymeric textile fibers and the like.

This migration to the surface is designated herein as "blooming". The problem of blooming is seen in polyester compositions containing flame retardant compounds not fully compatible with the polyester polymer in which said flame retardants are dispersed. The reason for the blooming is not fully understood but the effects, in most end uses, are undesirable.

The polymeric component of the compositions of this invention consists of polyesters such as polyethylene terephthalate, polybutylene terephthalate and the like, polyamides such as those prepared from hexamethylenediamine and adipic acid (referred to as Nylon 6,6), polycaprolactam (referred to as Nylon 6), bis(4-aminocyclohexyl) methane and dodecane adipic acid and the like; terpolymers of acrylonitrile, butadiene and styrene (referred to as ABS); acrylics such as polyacrylonitrile; modacrylics such as acrylonitrile copolymerized with vinyl or vinylidine halides; polyolefins such as polyethylene or polypropylene; polycarbonates, epoxy resins; polyurethanes and polyphenylene oxides.

The flame retardant component of the compositions of this invention as stated above is a compound of the formula

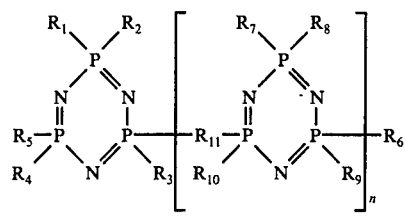

wherein each of $R_1$ to $R_{10}$ is a substituent of the formula

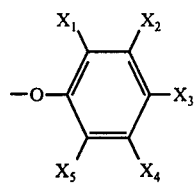

As indicated above the linking groups are derived from the following:

bisphenol A 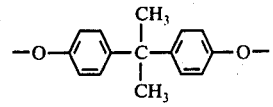

resorcinol 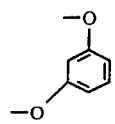

hydroquinone 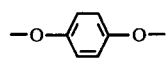

bisphenol S 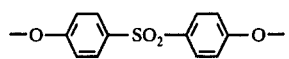

p,p'-dihydroxybiphenyl 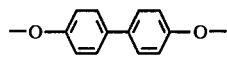

As indicated above $n$ is 1 or greater and describes the number of repeating units. It will be understood that $n$ as expressed herein represents the average number of repeating units and will generally be a number between 1 and 10 with both limits included.

It will be understood that $R_1$ to $R_{10}$ can be the same or different in any given compound of this invention.

Of the compounds of this invention compounds of the above formula wherein $R_1$ to $R_{10}$ are

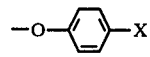

where X is bromine and $R_{11}$ is bisphenol A are preferred because of their compatibility with the various polymer systems and also because of their ease of preparation.

The flame retardant oligomer of the compositions of this invention are stable to light and normal processing conditions.

The oligomers of this invention are prepared by reacting hexachlorocyclotriphosphazene and an appropriate substituted phenol or phenols with an appropriate diol as is hereinafter described.

EXAMPLE 1

In a 3-necked, 3-liter round bottomed flask fitted with Dean-Stark trap and condenser, 0.80 mole of p-bromophenol is dissolved into one liter of toluene and is treated with 0.80 mole of KOH. The solution is refluxed for two hours and the resulting water is removed via the Dean-Stark trap. After cooling to room temperature 0.27 mole of hexachlorocyclotriphosphazene is added and the resultant mixture is refluxed for three hours. The mixture is cooled to room temperature and 0.27 mole of bisphenol A and 0.54 mole KOH is added following which reflux is restored and continued for an additional six hours. To the cooled solution is added 0.54 mole of p-bromophenol and 0.54 mole KOH and the mixture is again refluxed for six hours whereupon the solution is cooled to room temperature and treated with 400 ml of a 5% aqueous KOH solution. The toluene layer is treated with 20 g carbon black, dried over MgSO$_4$, filtered and stripped of solvent to give an oily tan product which, when dried in vacuo at 120° C. for 12 hours, becomes a hard solid, yield 190 g, mp 39°–42° C.

To confirm the identity of the product several methods of characterization were employed to determine $n$, the average number of trimeric phosphazene rings linked together in each oligomer.

Chlorine analysis was used to confirm that all P-Cl sites had been reacted. A further comparison of C, H, P and Br results can be used to interpolate $n$ of Example 1 as demonstrated in the following where $R_1$ to $R_{10}$ is a substituent of the formula

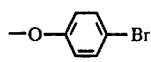

and $R_{11}$ is a substituent of the formula

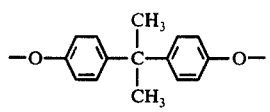

TABLE I

| | C | H | N | P | Br | Cl | Molecular Weight |
|---|---|---|---|---|---|---|---|
| | 37.05 | 2.07 | 3.60 | 7.96 | 41.08 | 0.00 | 1167 |
| $N_3P_3(O-\bigcirc-Br)_6$ | | | | | | | |
| n = 1 | 40.65 | 2.46 | 3.79 | 8.29 | 36.00 | 0.00 | 2226 |
| n = 2 | 41.68 | 3.19 | 3.84 | 8.48 | 34.05 | 0.00 | 4345 |
| n = ∞ | 44.64 | 2.88 | 4.00 | 8.86 | 30,.46 | 0.00 | $1049_n$ |
| Product of Example 1 | 41.85 | 2.25 | 4.00 | 8.79 | 34.52 | <0.3 | |

An assignment of $n = 2$ is consistent with the values for the oligomer of Example 1 by the above interpolation.

The molecular weight of the product of Example 1 is 3600 as determined ebullioscopically in toluene.

An alternate method of determining the value of $n$ is the use of proton nuclear magnetic resonance (nmr) spectroscopy when, as in Example 1, bisphenol A is the diol used in preparing the oligomer of this invention. The use of bisphenol A introduces aliphatic protons into the molecule and the value of $n$ can be determined by the ratio of integration for aromatic to aliphatic protons. In Table II, theoretical values of this ratio are listed for the different values of $n$ for the product of Example 1.

TABLE II

| n | No. of p-bromo-phenol | No. of Bis-phenol-A | No. of Aromatic H | No. of Aliphatic H | Ratio Aromatic: Aliphatic H |
|---|---|---|---|---|---|
| 0 | 6 | 0 | 24 | 0 | ∞ |
| 1 | 10 | 1 | 48 | 6 | 8 |
| 2 | 14 | 2 | 72 | 12 | 6 |
| ∞ | $4_n$ | $1_n$ | $24_n$ | $6_n$ | 4 |

The nmr spectrum of the product of Example 1 gives a ratio of 7.5. The upfield singlet occurs at 2.2δ and is assigned to the methyl groups of bisphenol A. The downfield multiplet reflects the aromatic protons of both p-bromophenol and bisphenol A. A ratio value of 7.5 corresponds to an average $n$ of 1 to 2 and is consistent with other determinations.

As indicated above all determinations conducted reflect an average value form. It is also probable that the actual oligomer is in fact a mixture of oligomers which when analyzed will give an $n$ value above 1. To confirm this assumption the product of Example 1 was subjected to gel permeation chromatography and found to be mostly a mixture of oligomers when $n = 1$ to 10. Therefore, it will be understood that such mixtures as well as the distinct oligomers are included within the scope of this invention.

EXAMPLE 2

In a 5-liter, 3-necked round bottomed flask fitted with a Dean-Stark trap, two condensers and overhead stirrer, 1.6 mole of p-bromophenol and 0.53 mole of hexachlorocyclotriphosphazene is dissolved into two liters of toluene. Then 16 moles of KOH pellets (85% KOH) is added, the mixture is stirred for 30 minutes at room temperature and is then heated to reflux and refluxed for three hours. The mixture is cooled to room temperature and 0.53 mole of bisphenol A is added and 1.06 mole of KOH pellets (85% KOH) is added being careful to avoid boil over. The solution is brought to reflux, taking care to avoid boil over, is refluxed for 24 hours and is cooled. An additional 1.06 mole of p-bromophenol and 1.06 mole KOH pellets (85% KOH) is added and the solution is refluxed for six hours, cooled to room temperature and filtered. The filtrate is washed with 5% aqueous KOH solution and the toluene layer is separated, treated with $MgSO_4$ (anhydrous) 25 grams and 20 grams of carbon black and is filtered to give a clear light brown solution. The toluene is stripped from the light brown solution leaving an oil which is dried at 120° C. under vacuum. The product, poly(tetrakisparabromophenoxybisphenol-A cyclotriphosphazene), has a melting point range of 70°–73° C. and $n = 1$ to 10.

Characterization was by the methods described in Example 1 based on the following data:

| C 41.68 | N 3.75 | Br 34.80 |
|---|---|---|
| H 2.75 | P 8.41 | Cl <0.3 | nmr ratio of aromatic to aliphatic protons is 4.86.

Molecular weight by ebullioscopic measurement in toluene is 3950.

EXAMPLES 3-11

In general, the procedure of Example 2 was followed but substituting the indicated phenol and diol for the p-bromophenol and the bisphenol-A, respectively. Final molar proportions are the same as in Example 2 although ratios at the various stages in the preparation may be varied to obtain products as indicated. The M.W. column indicates the molecular weight of the product as obtained by boiling point elevation in toluene.

| Ex. | Phenol | Diol | M.W. of Product | M.P. |
|---|---|---|---|---|
| 3 | p-bromophenol | o,o'-dihydroxy- | 1280 | 93–97° C. |
| 4 | phenol | bisphenol A | — | — |

-continued

| Ex. | Phenol | Diol | M.W. of Product | M.P. |
|---|---|---|---|---|
| 5 | p-bromophenol | bisphenol S | 1265 | <room temp. |
| 6 | p-bromophenol | 4,4-dihydroxy-biphenyl | 1680 | <room temp. |
| 7 | phenol | bisphenol A | 2200 | ≃room temp. |
| 8 | phenol | tetrabromo-bisphenol A | 740 | room temp. |
| 9 | p-bromophenol | hydroquinone | — | room temp. |
| 10 | p-bromophenol | resorcinol | — | room temp. |
| 11 | p-chlorophenol | bisphenol A | — | room temp. |

TESTS FOR FLAME RETARDANCY

Horizontal Burn Test Preparation of Test Films

A composition of this invention was prepared by intimately mixing a polymer powder and (substituted phenoxy)cyclotriphosphazeneoligomer and then melt pressing this mixture into an 8-mil film with a fiberglass fabric as support. (The fiberglass fabric is style #1562, 0.005 inch thick, from Burlington Glass Fabrics Co.).

The melt pressing was done as follows: Films three inches square were prepared using a "sandwich" technique. The appropriate opening was cut into a copper shim, 0.002 inches thick and six inches square. A four-inch square sheet of aluminum was placed on a Squeege plate cut to fit into the press. (The aluminum sheet had been pretreated with Dow Corning R-671 resin, air dried, then heated at 250° C. for one hour and at 300° C. for one-half hour, to facilitate removal of clear films.) The fiberglass fabric and shim were placed over the aluminum sheet and about 1.8 g. of dry blend of polymer and oligomer was spread within the opening. A second aluminum sheet and Squeege plate was placed on top. The sandwich was put into the press which was then barely closed with no pressure applied.

The sandwich was allowed to heat up until both plates of the mold registered 280° C. After waiting thirty seconds, the mold was released, then closed under approximately 500 lbs. pressure for thirty seconds. While releasing the pressure the sandwich was pulled out and immediately dropped into ice and water, quenching the film. The aluminum sheets were peeled off the shim, the film was cut from the shim, dried at 50° C. and stored in a desiccator until used.

TEST PROCEDURE

The following test procedure was followed to compare the burn rate and burn length of various films prepared as described above: Films 1¼ × 3 inches were cut from the pressed squares and mounted in a U-shaped clamp such that an area of 1 inch × 3 inches was exposed. Both ends of the film were exposed while the two sides were inhibited. The clamp was mounted horizontally in a burning chamber arranged to insure a constant updraft.

The film samples were ignited with a wooden match. At the half-inch mark (as designated by the sample holder), the stop watch was started. The burning rate is based on the time required for the flame to progress from a point 0.5 inches from the open end of the specimen to a point 0.5 inches from the clamped end of the specimen. The flame front usually moved forward smoothly.

In Table III the test compound is described in the first column on the basis of the phenol and diol which are reacted with the hexachlorocyclotriphosphazene, notation of "Control", means that the polymer alone without test compound was burned. The second column lists the percent loading, i.e., the amount of test compound hot pressed into the polymer on a W/W basis. The third column "Burn Rate" reports the velocity of the burn in inches per minute.

TABLE III

| Test Compound | % Loading W/W | Burn Rate (In./Min.) |
|---|---|---|
| Control | — | 3.16 |
| Blend of Examples 1-2 | 10 | 2.00 |
| Example 2 | 10 | 1.64 |
| Example 9 | 10 | 2.34 |
| Example 10 | 10 | 1.90 |
| Example 11 | 10 | 2.08 |

FF-3-71 TEST

A tightly constructed fabric (6.6 oz./yd.$^2$) of Dacron ® yarn containing poly(tetrakisparabromophenoxybisphenol-A cyclotriphosphazene) at loadings of 6.0 and 9.5% is tested in accordance with the standard for the flammability of children's sleepwear [DOC-FF-3-71].

Char length was reduced from 14.6 cm. ± 8.1 cm. to 6.9 cm. ± 1.5 cm. and no char length in excess of 9 cm. is observed compared to 4/12 full length burns in Dacron ®. Average flame time is reduced from 22.3 seconds for untreated fabric to 14.3 seconds in fabric made from yarn containing the poly(tetrakisparabromophenoxybisphenol-A cyclotriphosphazene). A reduction of the magnitude and intensity of the flame is also observed.

In addition to the above tests to determine flame-retardant effectiveness of compositions of an oligomer of this invention dispersed in a polymer, the resistance to blooming was also evaluated as follows. An oligomer of the following formula was employed in the tests:

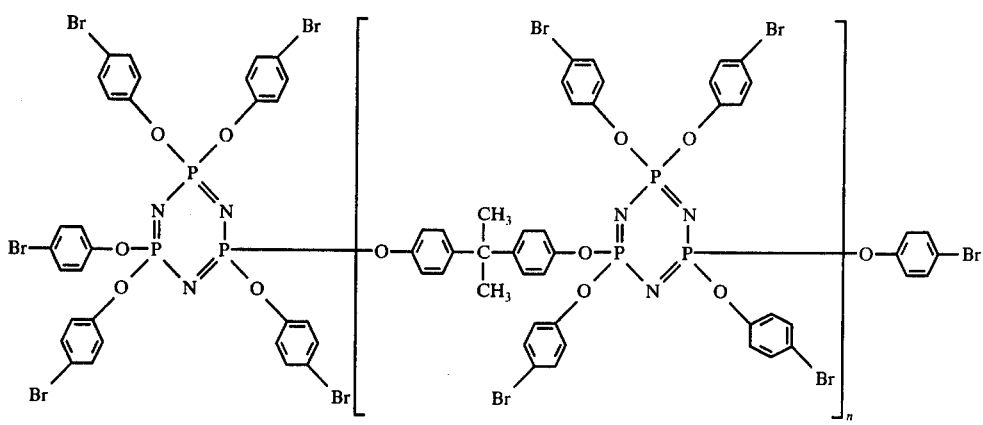

where $n$ is 1.5 average.

Yarns containing 3.8, 6.0 and 9.5% of the oligomer was exposed at 140° C., 170° C. and 200° C. for 15 minutes. A portion of each test yarn plus an unexposed control was then mock-dyed for 90 minutes at 100° C. with 20% (owf) butylbenzoate under typical atmospheric dyeing conditions.

A portion of thermally exposed yarn and unexposed control were suspended in an ultrasonic cleaner for five minutes at ambient temperature in benzene to remove any surface flame retardant. The analyses show no phosphorous loss, within experimental error, from any of the treatments. Data are summarized in Tables IV, V and VI.

TABLE IV
PHOSPHORUS CONTENT OF THERMALLY EXPOSED YARNS

| Oligomer Loading Treatment | 3.8% % P | 6.0% % P | 9.5% % P |
|---|---|---|---|
| None | 0.32 | 0.5 | 0.82 |
| 140° C./15 minutes | 0.31 | 0.55 | 0.82 |
| 170° C./15 minutes | 0.33 | 0.47 | 0.79 |
| 200° C./15 minutes | 0.31 | 0.55 | 0.82 |

TABLE V
PHOSPHOROUS CONTENT OF THERMALLY EXPOSED, MOCK-DYED YARN

| Oligomer Loading Treatment | 3.8% % P | 6.0% % P | 9.5% % P |
|---|---|---|---|
| No Heat/dye | 0.31 | 0.50 | 0.77 |
| 140° C./15 min./dye | 0.45* | 0.54 | 0.78 |
| 170° C./15 min./dye | 0.32 | 0.51 | 0.86 |
| 200° C./15 min./dye | 0.31 | 0.54 | 0.78 |

*aberration from other results not explainable.

TABLE VI
PHOSPHOROUS CONTENT OF BENZENE RINSED YARN

| Oligomer Loading Treatment | 3.8% % P | 6.0% % P | 9.5% % P |
|---|---|---|---|
| No Heat/rinse | 0.32 | 0.52 | 0.77 |
| 140° C./15 min./rinse | 0.35 | 0.56 | 0.82 |
| 170° C./15 min./rinse | 0.32 | 0.54 | 0.79 |
| 200° C./15 min./rinse | 0.32 | 0.55 | 0.78 |

From the above data it was concluded that the oligomer of this invention does not migrate to the surface of polyester yarn containing said oligomer when subjected to treatments that could be encountered during commercial use of said yarns.

What is claimed is:

1. A flame retardant polymeric composition comprising a polymer selected from the group consisting of polyester, polyamides, polycaprolactam, acrylic resins, modacrylic resins, acrylonitrile-butadiene-styrene terpolymers, polyolefins, polycarbonates, epoxy resins, polyurethanes and polyphenylene oxides and a flame-retardant effective amount of a compound of the formula

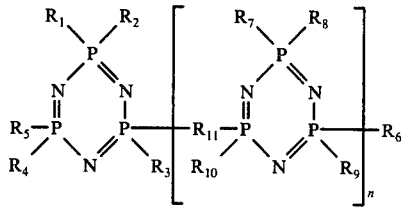

wherein each of $R_1$ to $R_{10}$ is a substituent of the formula

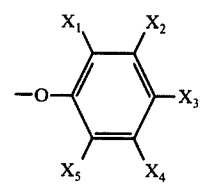

where
$X_1$ to $X_5$ is hydrogen, bromine and chlorine,
$R_{11}$ is a linking group derived from bisphenol A, resorcinol, hydroquinone, bisphenol S and p,p'-dihydroxybiphenyl, and
$n$ is a number from 1 to 10.

2. A method of decreasing the susceptibility of a polymer selected from the group consisting of polyesters, polyamides, polycaprolactams, acrylic resins, modacrylic resins, acrylonitrile-butadiene-styrene terpolymers, polyolefins, polycarbonates, epoxy resins, polyurethanes and polyethylene oxides to burn when exposed to open flame consisting of incorporating into the polymer a flame-retardant effective amount of a compound of the formula

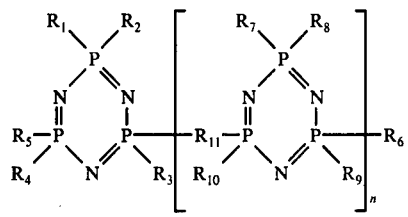

wherein each of $R_1$ to $R_{10}$ is a substituent of the formula

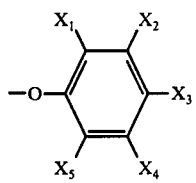

where
$X_1$ to $X_5$ is hydrogen, bromine and chlorine,
$R_{11}$ is a linking group derived from bisphenol A, resorcinol, hydroquinone, bisphenol S and p,p'-dihydroxybiphenyl, and
$n$ is a number from 1 to 10.

3. A flame retardant polymeric composition comprising
(a) a polymer selected from the group consisting of polyester, polyamide, acrylonitrile-butadiene-styrene terpolymer, acrylic, modacrylic and polyolefin; and
(b) a flame-retardant effective amount of a compound of the formula

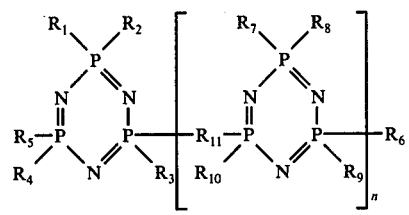

wherein each of $R_1$ to $R_{10}$ is

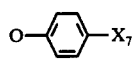

wherein
$X_7$ is selected from the group consisting of chlorine or bromine,
$R_{11}$ is a linking group derived from bisphenol A, resorcinol, hydroquinone, bisphenol S and p,p'-dihydroxybiphenyl, and
$n$ is a number from 1 to 10.

4. A flame retardant polymeric composition comprising
(a) a polymer selected from the group consisting of polyester, polyamide, acrylonitrile-butadiene-styrene terpolymer, acrylic resins, modacrylic resins, and polyolefin; and
(b) a flame-retardant effective amount of a compound of the formula

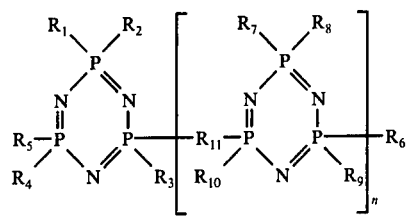

wherein
$R_1$ to $R_{10}$ is

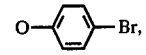

$R_{11}$ is bisphenol A.

5. A flame retardant polymeric composition comprising from 75 to 97% by weight of polyester and from 3 to 25% by weight of a phosphazene of the formula

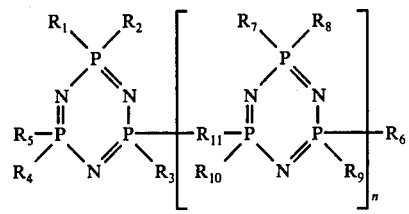

wherein each of $R_1$ to $R_{10}$ is a substituent of the formula

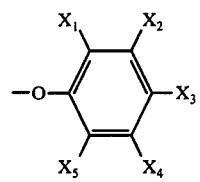

where
$X_1$ to $X_5$ is hydrogen, bromine and chlorine,
$R_{11}$ is a linking group derived from bisphenol A, resorcinol, hydroquinone, bisphenol S and p,p'-dihydroxybiphenyl, and
$n$ is the number 1 or greater.

6. A flame retardant polymeric composition comprising from 70 to 99% by weight polyolefin and from 1 to 30% by weight of a phosphazene of the formula

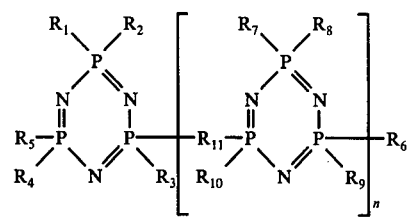

wherein each of $R_1$ to $R_{10}$ is a substituent of the formula:

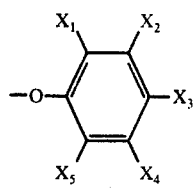

where
X₁ to X₅ is hydrogen, bromine and chlorine,
$R_{11}$ is a linking group derived from bisphenol A, resorcinol, hydroquinone, bisphenol S and p,p'-dihydroxybiphenyl, and
n is the number 1 or greater.

7. A flame retardant polymeric composition comprising from 88 to 99.5% by weight of polyamide and from 0.5 to 12% by weight of a phosphazene of the formula

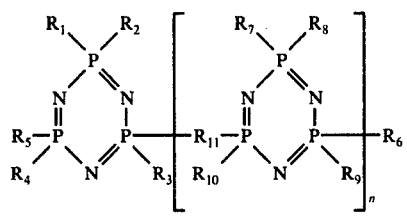

wherein each of $R_1$ to $R_{10}$ is a substituent of the formula

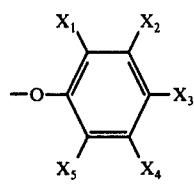

where
$X_1$ to $X_5$ is hydrogen, bromine and chlorine,
$R_{11}$ is a linking group derived from bisphenol A, resorcinol, hydroquinone, bisphenol S and p,p'-dihydroxybiphenyl, and
n is the number 1 or greater.

8. A flame retardant polymeric composition comprising from 70 to 95% by weight of acrylonitrile-butadiene-styrene terpolymer and from 5% to 30% by weight of an oligomer of the formula

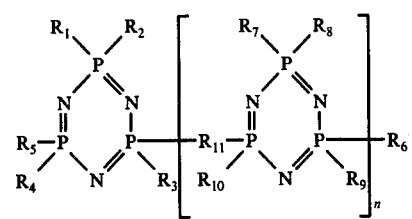

wherein each of $R_1$ to $R_{10}$ is a substituent of the formula

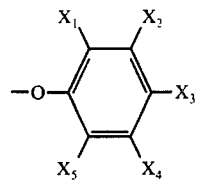

where
$X_1$ to $X_5$ is hydrogen, bromine and chlorine,
$R_{11}$ is a linking group derived from bisphenol A, resorcinol, hydroquinone, bisphenol S and p,p'-dihydroxybiphenyl, and
n is a number from 1 to 10.

9. A flame retardant polymeric composition comprising from 65 to 95% by weight of acrylic resins and from 5 to 35% by weight of an oligomer of the formula

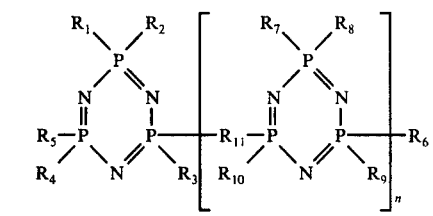

wherein each of $R_1$ to $R_{10}$ is a substituent of the formula

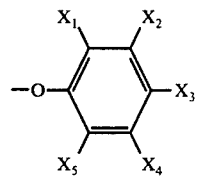

where
$X_1$ to $X_5$ is hydrogen, bromine and chlorine,
$R_{11}$ is a linking group derived from bisphenol A, resorcinol, hydroquinone, bisphenol S and p,p'-dihydroxybiphenyl, and
n is a number from 1 to 10.

10. A flame retardant polymeric composition comprising from 85% to 95% by weight modacrylic resins and from 5 to 15% by weight of an oligomer of the formula

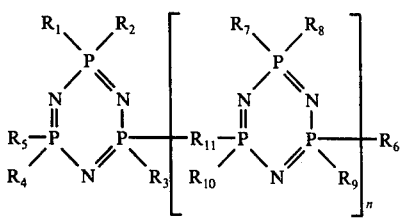

wherein each of $R_1$ to $R_{10}$ is a substituent of the formula:

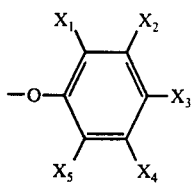

where $X_1$ to $X_5$ is hydrogen, bromine and chlorine, $R_{11}$ is a linking group derived from bisphenol A, resorcinol, hydroquinone, bisphenol S and p,p'-dihydroxybiphenyl, and $n$ is a number from 1 to 10.

11. A textile fiber formed from the composition of claim 5.

12. A textile fiber formed from the composition of claim 6.

13. A textile fiber formed from the composition of claim 7.

14. A textile fiber formed from the composition of claim 8.

15. A textile fiber formed from the composition of claim 9.

* * * * *